United States Patent [19]

Wardlaw

[11] Patent Number: 4,796,611
[45] Date of Patent: Jan. 10, 1989

[54] FRACTURE BRACE

[76] Inventor: Douglas Wardlaw, Mill of Monquich, Netherly, Stonehaven, United Kingdom

[21] Appl. No.: 79,091
[22] Filed: Jul. 29, 1987

[30] Foreign Application Priority Data

Jul. 31, 1986 [GB] United Kingdom ............ 8618651

[51] Int. Cl.$^4$ ............................................. A61F 5/04
[52] U.S. Cl. .................................... 128/87 R; 128/77; 128/88; 2/16
[58] Field of Search ................. 128/77, 87 R, 90, 88; 2/16, 22

[56] References Cited

U.S. PATENT DOCUMENTS

| 2,761,443 | 9/1956 | Parker | 128/91 R |
| 3,032,033 | 5/1962 | Ramirez | 128/90 |
| 4,013,070 | 3/1977 | Harroff | 128/77 X |
| 4,639,945 | 2/1987 | Betz | 2/22 |

FOREIGN PATENT DOCUMENTS

| 2052817 | 5/1972 | Fed. Rep. of Germany . | |
| 614510 | 12/1926 | France | 2/16 |
| 1233172 | 5/1976 | United Kingdom . | |

Primary Examiner—David A. Wiecking
Assistant Examiner—Moshe I. Cohen
Attorney, Agent, or Firm—Jacobs & Jacobs

[57] ABSTRACT

An orthopaedic brace for use in the treatment of fractures of a lower part of a limb such as the wrist or ankle is described. The brace comprises of two preformed portions, a first portion has two areas of high loading arranged distally and proximally on the portion and a second portion has one area of high loading at or near its center whereby the portions when fitted around a limb and fracture provide three point loading of the limb applied in two planes thereby maintaining the position of the fracture throughout the treatment period. In a preferred form the brace is used to treat Colles' fractrues whereby the first portion fits on the dorsal/radial part of the arm and the second portion fits on the anterior/ulnar part of the arm, the two portions being held in place by means of straps attached to the first portion.

13 Claims, 3 Drawing Sheets

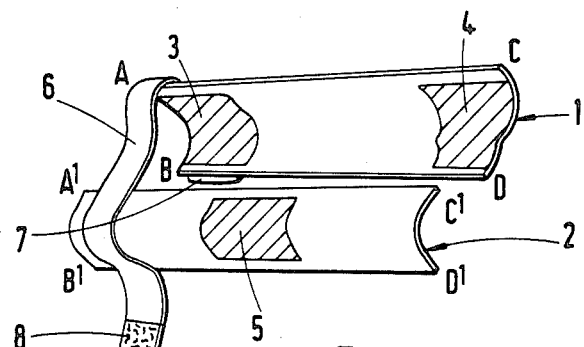
Fig.1
Fig.2
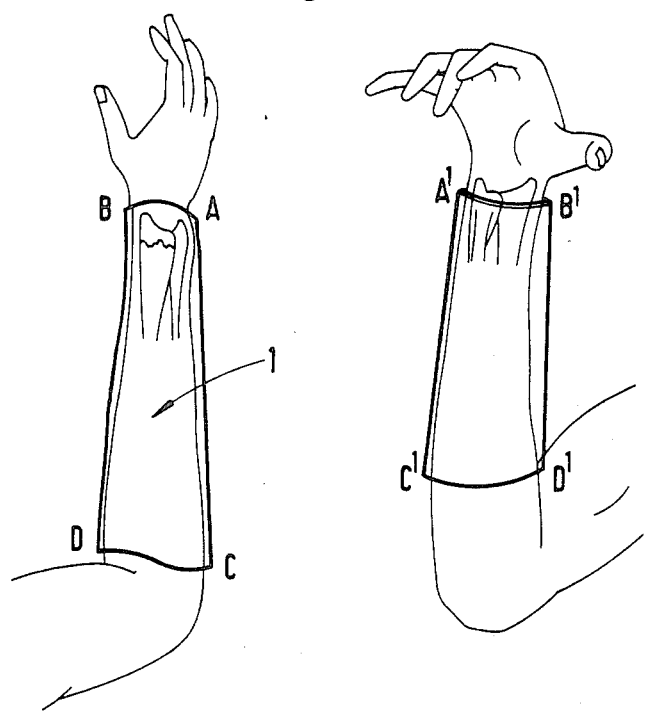

FRACTURE BRACE

The present invention relates to an orthopaedic brace for use in the treatment of fractures of a lower part of a limb such as the wrist or the ankle and in particular it relates to a brace suitable for the treatment of the so-called Colles' fracture of the wrist and of the fracture of the lateral malleolus in the ankle.

Fractures of the lower part of a limb, that is at the wrist or ankle are very common A Colles' fracture, for example, which involves the lower end of the radius accounts for 10–20% of all fractures seen in fracture clinics. The Colles' fracture can cause morbidity out of proportion to its presumed significance In most centres, the treatment of a Colles' fracture is carried out in the Accident and Emergency Department by relatively inexperienced personnel using the so-called Charnley dorsal/radial slab to immobilize the wrist after disimpaction and reduction of the fracture. This slab is conventionally formed from layers of plaster of Paris. Morbidity with this treatment is related to pain, stiffness, loss of function of the wrist and fingers after cast removal, and persistent deformity, all of which affect the ability to use the limb in the short term, followed by an often prolonged period of rehabilitation. It may also leave, in a small proportion of cases, a significant and permanent loss of function.

Similar problems have been observed in the treatment of fractures of the ankle which are treated by whole leg or below-the-knee casts formed from conventional plaster of Paris bandages In both cases it requires a degree of expertise to apply plaster of Paris bandages correctly so that the cast formed does not have to be replaced during the fracture healing period and so that the fracture heals with little or no deformity.

Alternatives to the plaster of Paris slab treatment of fractures have been suggested. These alternatives include internal fixation, percutaneous pin fixation and various fracture bracing techniques None of these methods showed a significant improvement over conventional treatments. In general existing fracture bracing techniques may allow earlier mobilisation of the fracture but they fail to maintain the fracture position adequately enough to allow significant long term advantage.

Recently materials have become commercially available which are thermoplastic and which are moldable or formable when heated to 40°–80° C., for example, by placing in an oven or hot water, by directing hot air against a sheet of the material or by using a special hot plate. These materials can be used to form braces to treat fractures. A typical thermoplastic material comprises linear polyester. Such material is mouldable when heated and retains the impressed configuration on cooling. A splint using this type of material is described in for example U.S. Pat. No 4,600,618.

I have now discovered a brace which is suitable for treating fractures of a lower part of a limb which mitigates the post-application problems described above. Surprisingly the same brace may be used for the treatment of fractures at both the wrist and the ankle. This brace can be made of a preformed material which does not need specialised equipment such as the heating equipment described above for its application and which does not require to be formed around the limb. The brace may be made in several sizes and in right and left handed forms and is adapted in shape so that the fracture position is maintained while at the same time it does not restrict movements at the joint thereby allowing early recovery of function and it maintains fracture reduction throughout the period of treatment. The morbidity due to deformity and long term restriction of movement is decreased. The construction and mode of application of the brace allows relatively inexperienced personnel to apply the brace safely whilst ensuring that the advantages described above are maintained.

Accordingly the present invention provides an orthopaedic brace suitable for the treatment of fractures of a lower part of a limb which brace comprises two preformed portions, a first portion which has two areas of high loading arranged distally and proximally on the portion and a second portion which has an area of high loading at or near its centre whereby the portions when fitted around the limb and fracture provide three point loading of the limb.

Accordingly in one preferred aspect the present invention provides an orthopaedic brace suitable for the treatment of Colles' fractures which brace comprises two preformed portions, a first portion which is adapted to fit on the dorsal/radial part of the arm and which has two areas of high loading arranged distally and proximally on the portion, and a second portion which is adapted to fit on the anterior/ulnar part of the arm, and which has an area of high loading at or near its centre whereby the portions when fitted about the arm provides three point loading of the forearm.

By arranged proximally and distally it is meant the areas are at or near to either end of the first portion. The distal area is conventionally regarded as that which is at the wrist or ankle and the proximal area is that which is towards the elbow or knee.

The displacement in fractures of the lower part of a limb is usually in two directions and as a result a remedial force should be provided to counter this. In my invention this remedial force is provided by three point loading which is operable in two planes. For example the displacement in a Colles' fracture is in both dorsal and radial directions and thus the loading of the distal fragment provided by the brace is in an anterior and ulnar direction so as to provide a remedial action.

Aptly the remedial force is provided by having areas of high loading on the inside surface of the two portions of the brace that is on the surface which faces towards the limb. These areas of high loading may be provided by having raised areas at appropriate places on the inside of each portion of the brace. These areas may be comprised of (a) indentations in the walls of the brace (b) thickened areas of material in the portions of the brace or (c) pads inserted or adhered to the inside of the portions of the brace Suitably the first portion of the brace carries raised areas at or near either end of the portion that is distally and proximally and the second portion of the brace carries a raised area at or near its centre. Each raised area aptly has a significant area so that localised pressure points are not created which could be deliterious Aptly the raised areas on the portions of the brace are arranged so that they do not coincide. This avoids clamping the limb over a local area between two raised areas on portions of the brace which could lead to a constriction of the circulation in the limb.

The first portion of the brace may be the longer portion carrying as it does two of the areas of high loading. This portion fits over one part of the limb but is short enough to avoid contacting a joint such as the knee or elbow and thus allows full movement of these joints with reduced risk of disturbing the brace. The first portion of the brace may be produced in different sizes to accommodate variations in the width of the limb as for example at the wrist and ankle and in different shapes to provide for right and left limbs. The first portion of the brace may be formed from a solid shell but more suitably may be perforated to provide holes for ventilation or may even comprise only the two pressure applying areas joined by rigid members such as rods. The second portion may be smaller than the first and the two portions may be arranged to engage with each other so that only one size of second portion need be used. This may be achieved by providing the first portion with extended walls whereby the second portion may be fitted within the first portion at various positions depending on the thickness of the forearm.

When the brace is used to treat a Colles' fracture the shape is such as to provide three point loading of the forearm so that there is loading of the distal end of the radius over a relatively wide area to prevent local pressure points The three point loading is applied by the brace at the dorsal and radial aspects of the lower wrist, the dorsal and radial aspects of the proximal forearm and at the anterior and ulnar aspects of the forearm midway between these points The brace is applied under a degree of tension and loading so that as the fracture swelling subsides and the bony fragments begin to heal, loading is maintained preventing redisplacement of the fracture.

Aptly the brace is preformed from a material which can not be altered once it assumes the correct proportions for the brace. Favourably, therefore, the brace may be formed from plaster of Paris or a fibre reinforced resin. Thermoplastic polymers such as those commonly used in mouldable splints such as polycaprolactone, polyethylene foam and the like may be used if precautions are taken to prevent the brace being altered by the patient or by the orthopaedic technician. Since the brace is supplied preformed and preferably cannot be altered, the brace may be provided in three or four sizes for each of the right and left arms.

The brace is, however, preferably formed from a plastics material.

It may be advantageous to have areas of a skin compatible pressure sensitive adhesive on the inside surface so that the brace may be adhered to the skin to prevent movement of the brace along the forearm as when for example a swollen fracture site returns to its normal size. Suitable adhesives will be those which are compatible with the skin and include natural rubber adhesives, polyvinyl alkylether adhesives and polyacrylate copolymer adhesives.

The first portion of the brace may carry attached to one edge thereof straps for holding the two portions of the brace together Suitably each strap has on its surfaces fastening means for mechanical interaction with a second surface, such pairs of interacting fastenings include hook and pile fastenings which are commonly known as "Velcro". The outer surface of the second portion also carries strips of this material The other edge of the first portion of the brace carries a buckle. To fasten the brace each strap is passed over the outer surface of the second portion to which it is fastened by means of the interacting fastenings then through the buckle and its end folded back to fasten to itself whereby the brace is held firmly around the limb. The brace can be applied under tension so that the brace does not become loose as any swelling associated with the fracture subsides The straps may be elasticised to enhance this effect Suitably the brace may carry two or three straps. When treating a fracture, the fracture is first reduced and a conventional orthopaedic adding is applied to the limb either as a single layer or as a multiple layer depending upon the expected fit between the brace and the limb. The first portion is placed on the limb, then the second portion is applied to the limb and the straps passed through the buckles to fasten the brace around the limb. The brace may be left in postion for the treatment period in which six weeks is a common period for a Colles' fracture.

In a second aspect of the present invention a thigh or an upper arm brace may be present and is attached to the frature brace by means of a hinge centred on the knee or elbow joint to allow free flexion and extension movements.

In another aspect the present invention provides a method of treating a fracture of a lower part of a limb by applying thereto a brace which comprises two preformed portions, a first portion which has two areas of high loading arranged distally and proximally on the first portion and a second portion which has an area of high loading at or near its centre whereby the portions when fitted around the limb and fracture provide three point loading of the limb. In a preferred form the brace is used to treat a Colles' fracture.

A specific embodiment of the invention will now be described by way of example with reference to the accompanying drawings in which FIG. 1 shows a perspective view of a Colles' fracture brace of the invention.

FIG. 2 shows the fracture reduction and application of the dorsal/radial portion of the brace.

Figure 3:
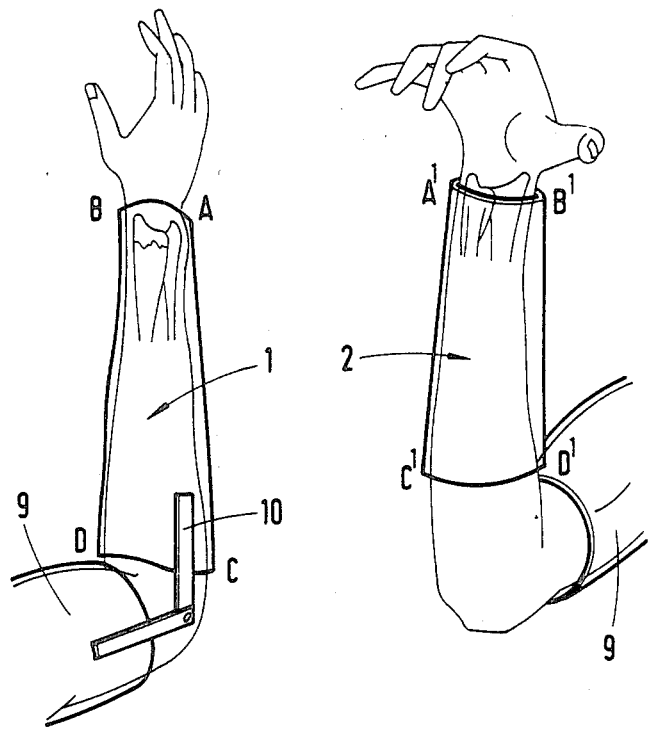
FIG. 3 shows the application of the anterior/ulnar portion of the brace and also illustrates the presence of the upper arm section.
Figure 4:
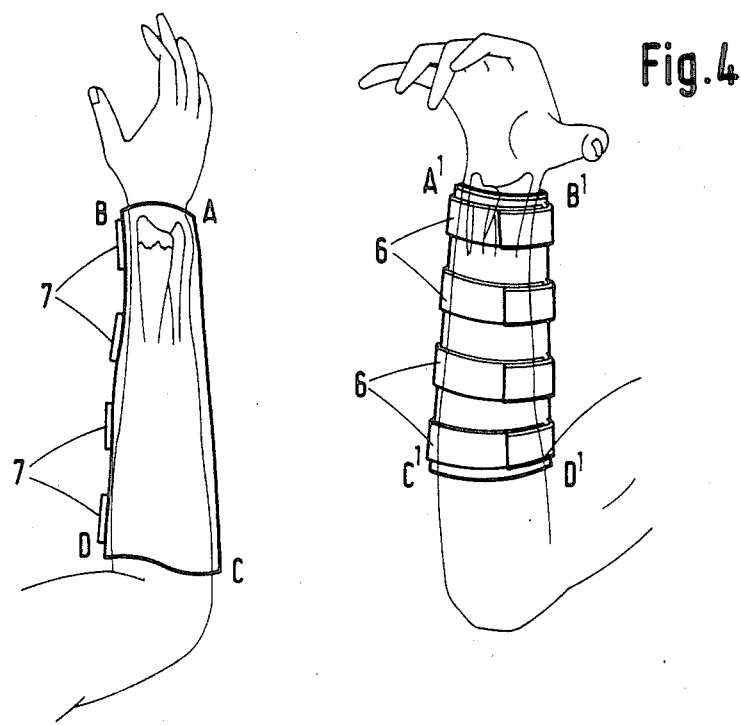
FIG. 4 shows the application of the interactive fastening on the brace.

FIG. 1 shows a brace comprising of two portions a first, dorsal/radial portion (1) and a second anterior/ulnar portion (2). The first portion (1) has at either end two straps (6) which carry on either side interactive fastening means. The two portions are applied so that the four corners (A, B, C, D) and (A', B', C', D') of each portion come together. The area of high loading on the dorsal/radial portion occurs distally at the raised area shown as shaded area (3) and proximally at the raised area shown as shaded area (4). The area of high loading on the anterior/ulnar portion occurs at the raised portion shown as the shaded area (5). The two portions of the brace are united by the straps (6) by passing the straps over interactive fastening means on the outer surface of the second portion of the brace and through the buckles (7) and folded back onto themselves onto "Velcro" fastenings on the other side of the straps (6). In use when the Colles' fracture has been reduced the arm may be covered by one or more layers of orthopaedic wadding and then the dorsal/radial portion (1) is first applied to the forearm as is shown in FIG. 2. The anterior/ulnar portion (2) is then also applied as is shown in FIG. 3. The straps (6), buckles (7) and "Velcro" fastenings (8) are done up as shown in FIG. 4 so that the brace is fitted in position maintaining the fracture in reduction while permitting free movement of the wrist and fingers.

FIG. 3 shows another embodiment of the invention in which an upper arm section (9) is present in the brace This section is connected to the dorsal/radial portion (1) by hinges (10).

Figure 5:
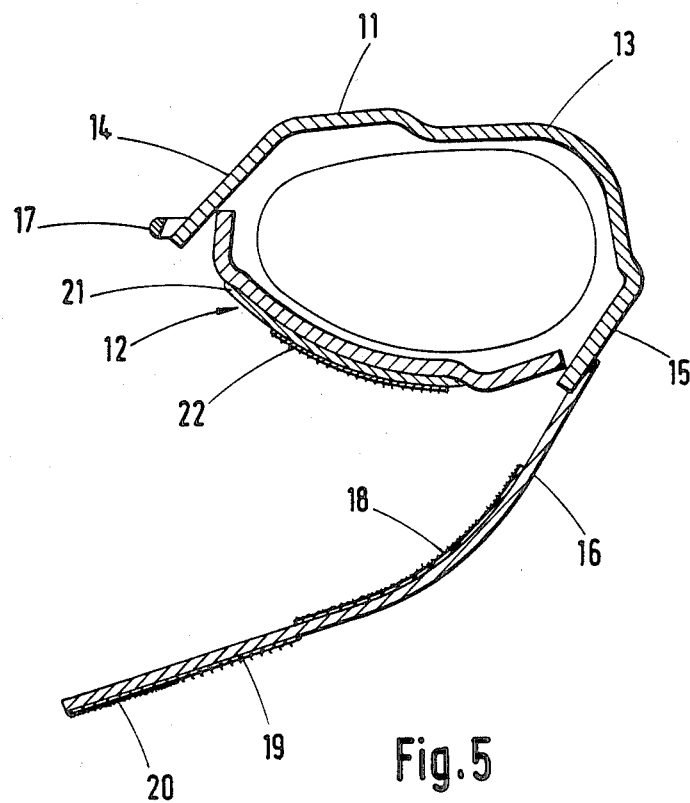
FIG. 5 shows a cross-section through a brace of present invention.

FIG. 5 shows a cross-section through a brace of the invention the first portion (11) has an area of high loading shown by the raised area (13). The walls (14, 15) of the portion (11) are substantially straight so that the second portion (12) can contact the walls over a range depending on the thickness of the limb around which the brace is placed. One wall of the first portion has attached to it at least two straps (16) (only one shown) which have areas of interactive fastening (18, 19, 20) on either side, the other wall carries a buckle (17). The second portion (12) has an area of high loading (21) which is at or near its centre. The second portion (12) has an area of interactive fastening (22) on its non-body contacting surface. On fitting around the limb the area of interactive fastening (18) engages with area (22) on the second portion. The remainder of the strap (16) is passed through the buckle (17) and folded back on its self so that areas (19) and (20) fasten to each other.

I claim:

1. An orthopaedic brace suitable for the treatment of fractures of a lower part of a limb which brace comprises two preformed portions of substantially equal length, one of said portions being larger than the other, said portions together extending substantially around the circumference of the limb, the first one of said portions having two areas of high loading arranged distally and proximally on the portion and the second one of said portions having an area of high loading at or near its centre, said areas of high loading being provided by raised areas on the inside surfaces of said first and second portions, whereby the portions when fitted around the limb and fracture provide three point loading of the limb.

2. A brace according to claim 1 in which the three point loading is applied in two planes whereby the position of the fracture is maintained throughout the treatment period.

3. A brace according to claim 1 in which the raised areas are provided as indentations in the walls of the first and second portions of the brace.

4. A brace according to claim 1 in which the raised areas are provided by thickened areas in the walls of the first and second portions of the brace.

5. A brace according to claim 1 in which the loading is provided by pads present at the appropriate positions on the first and second portions of the brace.

6. A brace according to claim 1 in which pressure sensitive adhesive areas are present on the inside surfaces of the first and second position of the brace whereby the brace may be adhered to the skin.

7. A brace according to claim 1 in which the brace is in a form which is suitable for application to the right side or which is suitable for application to the left side.

8. A brace according to claim 1 in which the brace is formed from a plastics material.

9. A brace according to claim 8 in which the brace permits free movement of wrist and elbow.

10. A brace according to claim 1 which is suitable for the treatment of Colles' fractures whereby the first portion is placed over the dorsal/radial part of the forearm and the second portion is placed over the anterior/ulnar part of the forearm.

11. A brace according to claim 10 which additionally comprises an upper arm section which is connected to the first portion of the brace by means of a hinge.

12. A method of treating a fracture of a lower part of a limb by applying thereto a brace which comprises two preformed portions of substantially equal length, one of said portions being larger than the other, said portions together extending substantially around the circumference of the limb, the first one of said portions having two areas of high loading-arranged distally and proximally the first portion and the second one of said portions having an area of high loading at or near its centre, said areas of high loading being provided by raised areas on the inside surfaces of said first and second portions, whereby the portions when fitted around the limb and fracture provide three point loading of the limb.

13. A method according to claim 12 in which the fracture is a Colles' fracture and in which the first portion is placed over the dorsal/radial part of the forearm and the second portion is placed over the anterior/ulnar part of the forearm.

* * * * *